(12) United States Patent
Biotti et al.

(10) Patent No.: US 10,900,703 B2
(45) Date of Patent: *Jan. 26, 2021

(54) REFRIGERATION APPLIANCE AND METHOD FOR OPERATING SUCH APPLIANCE

(71) Applicant: WHIRLPOOL CORPORATION, Benton Harbor, MI (US)

(72) Inventors: Carolina Biotti, Comerio (IT); Raffaele Paganini, Comerio (IT); Davide Parachini, Comerio (IT); Maria P. Pirovano, Comerio (IT)

(73) Assignee: Whirlpool Corporation, Benton Harbor, MI (US)

( * ) Notice: Subject to any disclaimer, the term of this patent is extended or adjusted under 35 U.S.C. 154(b) by 396 days.

This patent is subject to a terminal disclaimer.

(21) Appl. No.: 15/264,961

(22) Filed: Sep. 14, 2016

(65) Prior Publication Data

US 2017/0003065 A1 Jan. 5, 2017

Related U.S. Application Data

(63) Continuation of application No. 14/717,509, filed on May 20, 2015, now Pat. No. 9,497,977.

(30) Foreign Application Priority Data

May 21, 2014 (EP) ..................... 14169369

(51) Int. Cl.
*A61L 2/20* (2006.01)
*A61L 9/015* (2006.01)
(Continued)

(52) U.S. Cl.
CPC ............ *F25D 17/042* (2013.01); *A23B 7/055* (2013.01); *A23B 7/144* (2013.01); *A61L 2/00* (2013.01);
(Continued)

(58) Field of Classification Search
CPC ..................................................... F25D 17/042
(Continued)

(56) References Cited

U.S. PATENT DOCUMENTS 3,543,021 A * 11/1970 Scarborough, Sr. ...... A23L 3/28
250/372
6,967,008 B1 * 11/2005 Barnes .................. A01M 29/12
422/121

(Continued)

FOREIGN PATENT DOCUMENTS

JP 06153789 A 6/1994
JP 2010054092 A 3/2010
(Continued)

OTHER PUBLICATIONS

European Patent Office, European Search Report for European Patent Application No. 14169369.7, dated Oct. 10, 2014, 6 pgs.
(Continued)

*Primary Examiner* — Holly Kipouros
(74) *Attorney, Agent, or Firm* — Price Heneveld LLP

(57) ABSTRACT

A refrigeration appliance comprises a cavity in which an ozone generating device is placed. The ozone generating device is configured to maintain in the cavity a concentration of ozone between 0.04 and 0.12 ppm, more preferably between 0.06 and 0.1 ppm.

17 Claims, 3 Drawing Sheets

(51) Int. Cl.
    *F25D 11/00*     (2006.01)
    *A23B 7/144*     (2006.01)
    *F25D 17/04*     (2006.01)
    *F25D 25/02*     (2006.01)
    *A61L 9/00*     (2006.01)
    *A61L 2/00*     (2006.01)
    *A23B 7/055*     (2006.01)

(52) U.S. Cl.
    CPC ............... *A61L 2/202* (2013.01); *A61L 9/00* (2013.01); *F25D 25/025* (2013.01); *A23V 2002/00* (2013.01); *F25D 2317/0416* (2013.01)

(58) Field of Classification Search
    USPC .......................................................... 422/29
    See application file for complete search history.

(56) References Cited

U.S. PATENT DOCUMENTS

| | | | |
|---|---|---|---|
| 2002/0083724 A1* | 7/2002 | Tarlow | .................. A23L 3/3409 62/131 |
| 2006/0130498 A1 | 6/2006 | Joshi et al. | |
| 2010/0236269 A1 | 9/2010 | Mamemoto | |
| 2010/0243767 A1* | 9/2010 | Mori | ....................... A23L 3/375 239/691 |
| 2013/0059047 A1 | 3/2013 | Arrigo | |
| 2015/0210460 A1 | 7/2015 | Cherry | |
| 2015/0369530 A1* | 12/2015 | Bormann | .............. F25D 23/067 312/404 |

FOREIGN PATENT DOCUMENTS

| | | |
|---|---|---|
| WO | 2014070867 A1 | 5/2014 |
| WO | 2014154563 A1 | 10/2014 |

OTHER PUBLICATIONS

Ali et al., Effect of ozone pre-conditioning on quality and antioxidant capacity of papaya fruit during ambient storage, Jul. 17, 2013, Food Chemistry, pp. 19-26.

Tzortzakis et al., Deployment of low-level ozone-enrichment for the preservation of chilled fresh product, 2007, Postharvest Biology and Technology, vol. 43, pp. 261-270.

* cited by examiner

REFRIGERATION APPLIANCE AND METHOD FOR OPERATING SUCH APPLIANCE

CROSS-REFERENCE TO RELATED APPLICATIONS

This application is a continuation of U.S. patent application Ser. No. 14/717,509, filed on May 20, 2015, now U.S. Pat. No. 9,497,977, issued on Nov. 22, 2016, entitled "REFRIGERATION APPLIANCE AND METHOD FOR OPERATING SUCH APPLIANCE," which claims priority to European Patent Application No. EP14169369.7, filed on May 21, 2014, entitled "REFRIGERATION APPLIANCE AND METHOD FOR OPERATING SUCH APPLIANCE," the disclosures of which are incorporated herein by reference in their entirety.

BACKGROUND OF THE INVENTION

The present invention relates to a refrigeration appliance comprising a cavity in which an ozone generator is placed.

Interest in ozone has expanded in recent years in response to consumer demands for 'greener' food additives, regulatory approval and the increasing acceptance that ozone is an environmentally friendly technology. The multi functionality of ozone makes it a promising food processing agent. Excess ozone auto decomposes rapidly to produce oxygen and thus leaves no residues in foods from its decomposition. In particular, the US Food and Drug Administration (FDA)'s rulings on ozone usage in food have resulted in increased interest in potential food applications worldwide.

The effectiveness of ozone against microorganisms present in food systems depends on several factors including the amount of ozone applied, the residual ozone in the medium and various environmental factors such as medium pH, temperature, relative humidity, additives and the amount of organic matter surrounding the cells.

The use of ozone in the processing of foods has recently come to forefront, as a result of the approval by the FDA to use ozone as an antimicrobial agent for food treatment, storage, and processing.

Generally ozone is used in water treatment, sanitizing, washing and disinfection of equipment, odor removal, and fruit, vegetable, meat and seafood processing as an antioxidant.

Existing solutions on the market present the ozone device applied on the whole cavity of the refrigerator to improve air quality by odor removal and reduced microbial growth.

The main outcomes of such known solutions are related to the control and removal of ethylene for ripening fruits through the use of ozone, sterilization, implementation design, device components, and ozone device structure.

JP 06-153789 discloses a method for removing ethylene in a storehouse in which ozone is used for ethylene decomposition.

JP 2010-054092 shows a refrigerator with an ozone generating device arranged in a vegetable compartment. This document is silent about affective ozone concentration.

It is an object of the present invention to provide a refrigeration appliance with a device able to remove or reduce the residues of pesticides and microorganisms present on the surfaces of food items during storage by the ozone emission and in the meanwhile maintain their natural quality (color, ripening, freshness, and nutritional aspects) thanks to a new specific duty cycle treatment able to manage the ozone generation to allow food treatment without impacting food sensorial and nutritional quality. By using a certain ozone concentration the applicant has discovered surprising results in the maintenance of high levels of vitamin contents, particularly vitamin C content, for long storage periods in the cavity of the refrigerator.

The solution according to the invention is preferably integrated into a dedicated compartment for fresh fruits and vegetables (without packaging) in the refrigerator.

There are other additional benefits in using a certain ozone concentration, and they are related to keep food quality by microbial reduction; improve air quality by odor removal/reduce cross contamination and delay the ripening process by ethylene oxidation, while minimizing the oxidative process causing food deterioration.

BRIEF SUMMARY OF THE INVENTION

These and other features, advantages, and objects of the present invention will be further understood and appreciated by those skilled in the art by reference to the following specification, claims, and appended drawings.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown. Drawings are not necessary to scale. Certain features of the invention may be exaggerated in scale or shown in schematic form in the interest of clarity and conciseness.

DETAILED DESCRIPTION

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In this specification and the appended claims, the singular forms "a," "an" and "the" include plural reference unless the context clearly dictates otherwise.

With reference to the drawings, an ozone generating device 10 is placed in a specific sealed housing 12 and fixed on a rear wall 14 of an inner liner of a fresh food compartment A of a refrigerator. A consumer should not be able to remove the plastic housing 12 by hand. Such housing 12 is placed in the upper part of a crisper drawer D covered by a glass shelf S to permit a good mixing with the air in the drawer in the real time. If the drawer D isn't sealed by the upper shelf S the potential benefits are lower for food items inside. Ozone is therefore in direct contact on food surface. The ozone generating device 10 is mounted on the rear wall 14 of the liner in correspondence with a notch 13 provided in an upper rear wall of a crisper drawer D, so that the ozone generated by the ozone generating device 10 is confined in the crisper drawer D.

Figure 5:
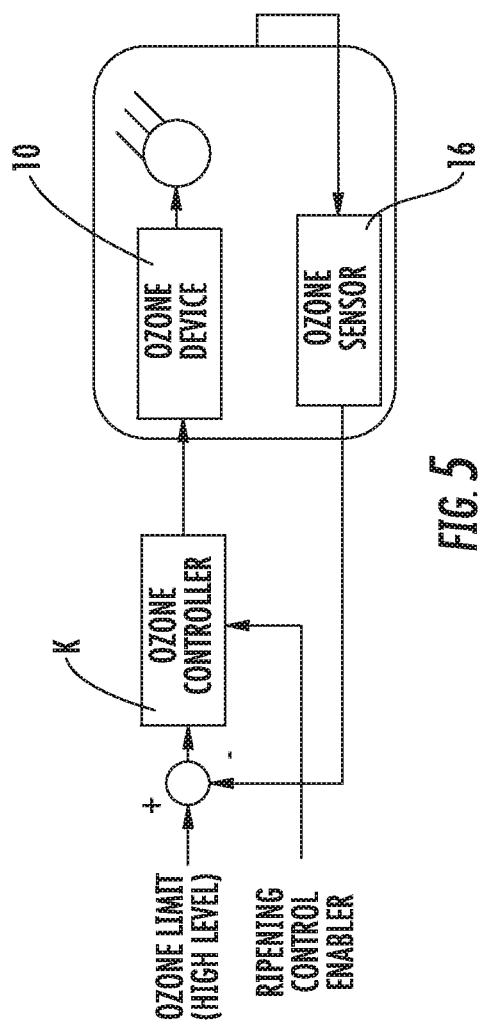
FIG. 5 shows an example of ozone generation control.
Figure 6:
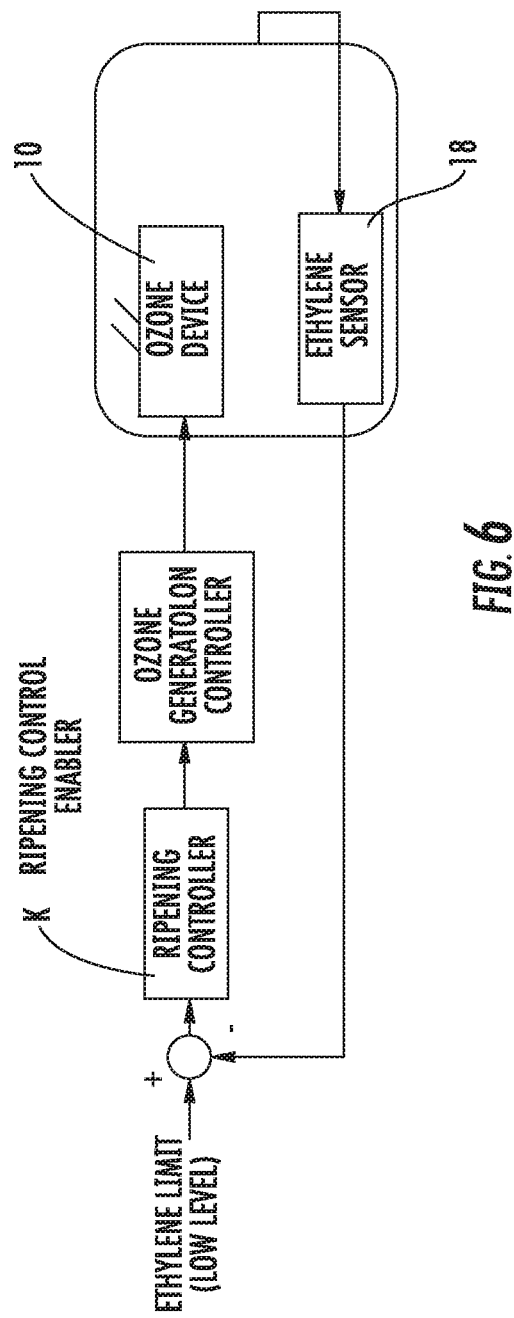
FIG. 6 shows an example of ripening control system according to the invention.

Besides the ozone device, the housing can be also equipped with an additional ozone sensor 16 (FIG. 5) and an ethylene sensor 18 (FIG. 6).

According to a specific feature of the invention, the duty cycle of the ozone device 10 produces an average of ozone concentration between 0.04 ppm and 0.12 ppm, preferably between 0.05 ppm and 0.11 ppm, with an ideal value around 0.08 ppm. At this concentration, ozone is able to act on cell membranes killing microorganisms without impact on nutritional aspects.

In tests carried out by the Applicant, the above concentration between 0.05 ppm and 0.11 ppm has shown to be the optimal one since it permits one to reach good microbial reduction and lower vitamin C reduction.

Lower ozone concentrations, i.e. <0.05 ppm, lead to no benefits: food items show the same performances as the ones stored in standard condition, the same as in absence of ozone.

With higher concentrations, i.e. higher than 0.1 ppm and particularly between 0.11 ppm and 4 ppm, consumer perceives the ozone odor and food presents fast decay in oxidative process (vitamin C, pigments . . . ), even if a reduced microbial growth is nevertheless assured.

Figure 1:
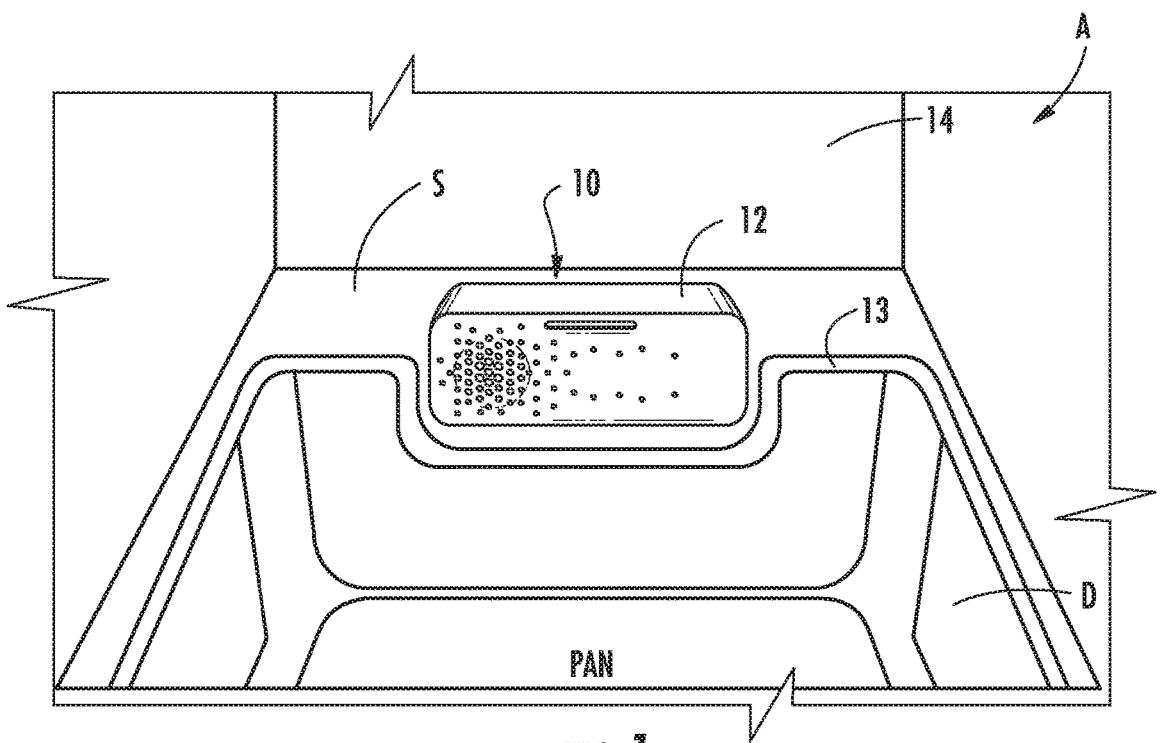
FIG. 1 is a perspective view of a portion of a refrigerator according to the invention.

To test the benefits of the optimal concentration of the ozone, it is necessary to drive the ozone generating device 10 with a proper duty cycle. A reference test procedure has been developed by the applicant in order to measure trade off tests on microbial and nutritional aspects considering an ozone device 10 that has been placed in the upper part of the crisper drawer D as shown in FIG. 1; the ozone concentration in such tests was constantly monitored using a portable ozone detector.

To define the ozone concentration, strawberry samples have been selected due to their higher perishable characteristic; they have been placed in a crisper bin inside the refrigerator at 5° C., 80% RH and endowed with the ozone device 10.

A relevant number of tests had been performed, and in particular a specific analysis had been evaluated. Microbial growth and vitamin C variation were estimated during the course of the experiment. Four different ozone concentrations have been used: reference value (without ozone activation), 0.012 ppm, 0.08 ppm, 0.12 ppm.

Generally, the higher the ozone concentration, the higher the microbial growth reduction, and the higher the vitamin C variation.

Figure 2:
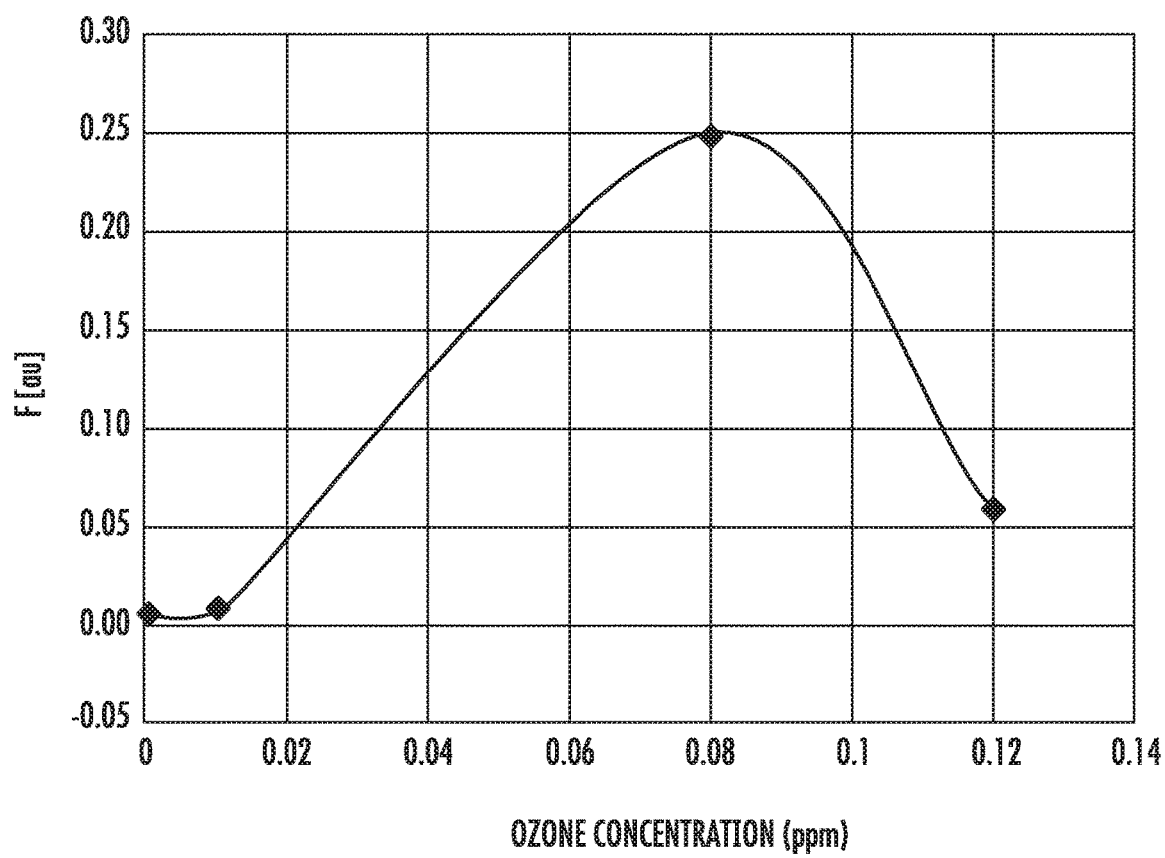
FIG. 2 is a graph showing the behavior of a function linking the ozone concentration to microbial growth and vitamin C variation.

Graph of FIG. 2 summarizes the trade-off between microbial growth, vitamin C variation and ozone concentration by a specific function F:

$$e - \frac{\frac{(\text{Vitamin } Co - \text{Vitamin } C)^{\wedge}2}{\delta^{\wedge}2}}{\log(UFC)}$$

Where:

Vitamin Co=initial vitamin C concentration in strawberries (mg/100 g sample)

Vitamin C=vitamin concentration at the end of storage (mg/100 g sample)

Sigma=Vitamin C variation that could be tolerated in the search of the optimal value Log (UFC)=Unit Formant Colonies, bacterial growth In ideal conditions vitamin C variation is close to zero and the ideal UFC (microbial growth) is low. The mathematical function that summarizes vitamin C variation and microbial growth is shown in FIG. 2. The above trade-off is reached at about 0.08 ppm of ozone concentration.

Other tests have been carried out by the Applicant to validate the trade-off target. In particular strawberries and tomatoes had been evaluated with a specific duty cycle that is able to generate 0.08 ppm. A comparison of performances was carried out on samples stored in the crisper bin endowed with ozone generator device 10 versus those placed into traditional crisper drawer without ozone generator. Food quality parameters have been observed for 14 days of storage in the crisper drawer.

Figure 3:
FIG. 3 is a graph showing the results for microbial growth for strawberries in a crisper of a traditional refrigerator and in a refrigerator according to the invention.

FIG. 3 presents the results for microbial growth for strawberries after 12 days of storage in the crisper bin D with and without ozone treatment.

By applying the optimal concentration, as shown in FIG. 3, ozone is able to reduce 2 logarithm units of the microbial growth every day of test.

In samples stored in standard conditions (no ozone), it is evident from the increase of the concentration value above $10^5$ UFC/g that white mold is present. This occurs after 6 days test; the same results have been achieved in tester condition after 12 days.

On the other hand the vitamin C variation is lower in samples stored in contact with ozone treatment.

Figure 4:
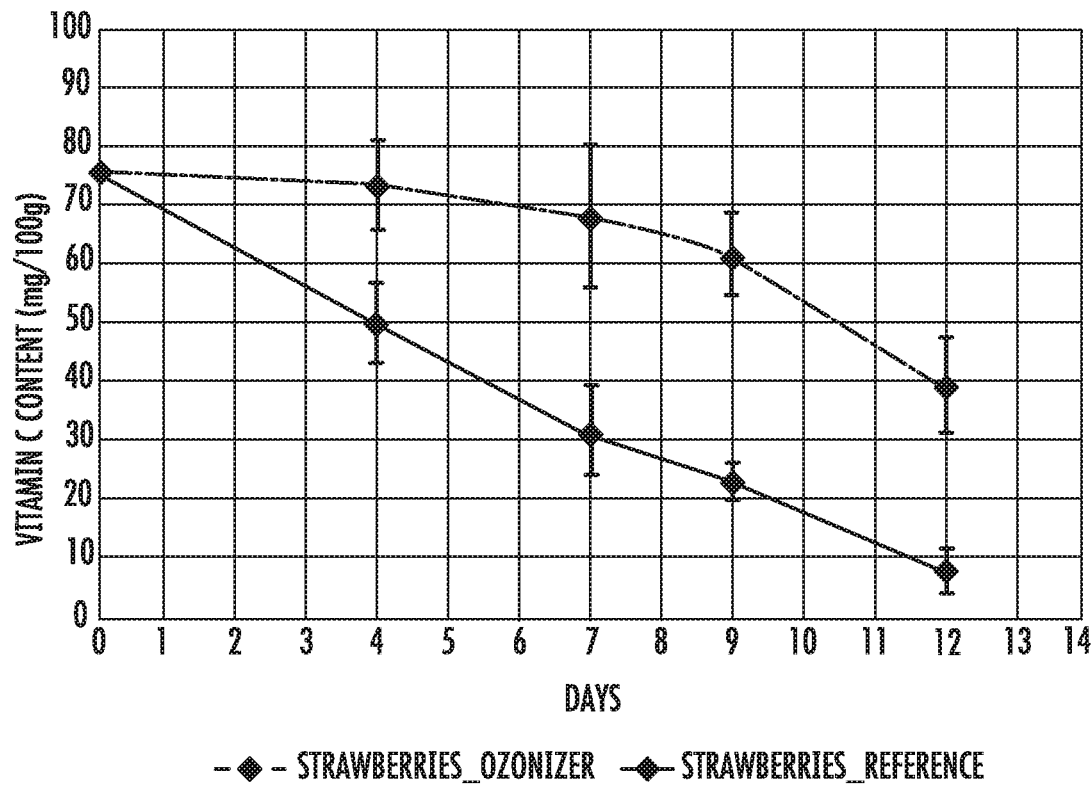
FIG. 4 is a graph showing how the vitamin C decay in a reference fresh food (strawberries) is slowed down in a refrigerator according to the invention.

FIG. 4 shows vitamin C content in strawberries stored in a crisper bin with ozone generator 10 vs. the standard one after 12 days.

By applying the optimal concentration, ozone is able to slow down the vitamin C decay.

In samples stored in standard conditions (no ozone), it is evident there is a fast decay in terms of vitamin C content.

In this way it is possible to prolong shelf life of foodstuff, reduce bacterial growth, and maintain the same nutritional quality.

According to a preferred embodiment of the invention, the current drawer and inner liner are modified and sensors are added in the lid S.

Ozone sensor 16 and ethylene sensor 18 (FIGS. 5 and 6) can be designed in a compact device (unique package) to save space and simplify cabling process.

The ozone sensor 16 is able to monitor the ozone concentration and sends an input to a control system K able to modulate the ozone generation and in case to stop it when the ozone threshold is reached.

There is no direct contact between the system (ozone generator 10 and sensors 16, 18 are placed in the housing 12) and consumer; when the drawer D is open the ozone generator 10 is switched off automatically.

Ozone is a powerful oxidizer that can also remove odors molecules and ethylene prolonging the storage time. The ethylene sensor 18 is able to monitor the ethylene production. It is preferably an electrochemical sensor for ethylene monitoring and it sends an input to switches on the device 10 when the ethylene reaches a predetermined threshold. Besides controlling the ethylene concentration, ozone is also monitored. In case ozone level reaches a predetermined limit, the system is blocked even if the ethylene concentration is still high.

The ozone device 10 is switched ON during storage to slow down the ripening in fruits when the ethylene sensor achieves a predetermined threshold (this can be managed by a specific algorithm that monitors the ethylene concentration).

The user interface of the refrigerator comprises a specific button or the like to allow the user to activate the ozone control (ozone generation system), with a LED light used as a feedback to show that the ozone generation is carried out.

Even if in the above description the ozone generator 10 has been shown as confined in the space of the crisper drawer D, it can also be associated to the entire cavity of the refrigerator or to another sub-compartment thereof.

The invention claimed is:

1. A refrigeration appliance comprising:
a crisper drawer defining a cavity and having a rear wall, the crisper drawer sealed by a glass shelf;
a sealed housing positioned within the cavity and covered by the glass shelf, wherein the sealed housing is coupled with the rear wall of the crisper drawer;
an ozone generating device positioned within the sealed housing, wherein the ozone generating device is configured to maintain a concentration of ozone in the cavity; and
a sensor operably coupled with the ozone generating device, wherein the sensor is at least partially positioned within the sealed housing.

2. The refrigeration appliance according to claim 1, wherein the ozone generating device is configured to maintain the concentration of ozone in the cavity having a value between about 0.06 and about 0.1 ppm.

3. The refrigeration appliance according to claim 1, wherein the sealed housing is mounted on the rear wall of the crisper drawer in correspondence with a notch provided in an upper portion of the rear wall of the crisper drawer, and further wherein the crisper drawer is sealed so that the ozone generated by the ozone generating device is confined in the crisper drawer.

4. The refrigeration appliance according to claim 1, wherein the sensor is an ozone sensor for adjusting the ozone concentration to a desired value.

5. The refrigeration device according to claim 1, wherein the sensor is an ethylene sensor for adjusting the ozone concentration to a desired value.

6. The refrigeration device according to claim 1, wherein the sensor includes an ozone sensor and an ethylene sensor for adjusting the ozone concentration to a desired value.

7. The refrigeration appliance according to claim 1, wherein the ozone generating device deactivates when the crisper drawer is in an open position.

8. A refrigeration appliance comprising:
a first housing defining a cavity and having a rear wall, the first housing selectively movable between a sealed position and an open position, wherein the first housing is substantially sealed by a lid when in the sealed position;
a second sealed housing positioned within the cavity, and coupled to the rear wall of the first housing;
at least one sensor positioned within the second sealed housing, the at least one sensor configured to detect one of ethylene concentrations and ozone concentrations; and
an ozone generating device positioned within the second sealed housing and coupled to the at least one sensor, the ozone generating device configured to maintain in the cavity a concentration of ozone having a value between about 0.05 and about 0.10 ppm, and further wherein the maintained concentration of ozone inhibits microbial growth and preserves nutritional quality of food.

9. The refrigeration appliance of claim 8, wherein the at least one sensor includes one of an ethylene sensor and an ozone sensor.

10. The refrigeration appliance of claim 8, wherein a control system is operably coupled to the ozone generating device and the at least one sensor.

11. The refrigeration appliance of claim 10, wherein the ozone generating device is configured to shut off when the first housing is in the open position.

12. The refrigeration appliance of claim 8, further comprising:
a user interface, the user interface including an input for a user to activate the ozone generating device, wherein the user interface further includes an output to indicate the activation of the ozone generating device.

13. A refrigeration appliance comprising:
a first housing defining a cavity and having a rear wall, the first housing movable between a sealed position and an open position, wherein the first housing is sealed by a shelf when the first housing is in the sealed position;
a second sealed housing positioned within the cavity of the first housing;
a sensor positioned within the second sealed housing;
an ozone generating device positioned within the second sealed housing and coupled to the sensor;
a control system operably coupled to the ozone generating device and the sensor; and
a user interface, the user interface including an input for a user to activate the ozone generating device, wherein the user interface further includes an output to indicate the activation of the ozone generating device.

14. The refrigeration appliance according to claim 13, wherein the ozone generating device is configured to shut off when the first housing is in the open position.

15. The refrigeration appliance according to claim 13, wherein the sensor is one of an ethylene sensor and an ozone sensor.

16. The refrigeration appliance according to claim 13, wherein the second sealed housing is coupled to the rear wall.

17. The refrigeration appliance according to claim 13, wherein the second sealed housing is positioned on the shelf.

* * * * *